United States Patent [19]

Löhn et al.

[11] 4,382,786
[45] May 10, 1983

[54] DENTAL HANDPIECES WITH SUPPLIED OPERATING MEDIA

[75] Inventors: Gerd Löhn; Stefan Beier, both of Biberach, Fed. Rep. of Germany

[73] Assignee: Kaltenbach & Voight GmbH & Co., Biberach, Fed. Rep. of Germany

[21] Appl. No.: 296,157

[22] Filed: Aug. 25, 1981

[30] Foreign Application Priority Data

Sep. 16, 1980 [DE] Fed. Rep. of Germany ....... 3034930

[51] Int. Cl.³ .......................... A61C 1/10; A61C 1/12
[52] U.S. Cl. ...................................... 433/85; 433/28; 433/100; 433/126
[58] Field of Search ................... 433/85, 126, 100, 99, 433/28, 80, 82, 84; 128/224, 229

[56] References Cited

U.S. PATENT DOCUMENTS

| | | | |
|---|---|---|---|
| 3,673,709 | 7/1972 | Page | 433/28 |
| 3,702,940 | 11/1972 | Stewart | 433/28 |
| 4,080,737 | 3/1978 | Fleer | 433/126 |
| 4,205,236 | 5/1980 | Goof | 433/99 |
| 4,217,101 | 8/1980 | Loge | 433/126 |

FOREIGN PATENT DOCUMENTS 1766671 11/1979 Fed. Rep. of Germany ........ 433/99

Primary Examiner—Gene Mancene
Assistant Examiner—John J. Wilson
Attorney, Agent, or Firm—Scully, Scott, Murphy & Presser

[57] ABSTRACT

A dental treatment installation comprising at least one dental handpiece having an air operated drive motor and an outlet for discharging operating media used for dental purposes, a spray handpiece, a control arrangement for controlling the supply of operating media to the handpieces, and a storage device for the handpieces having storage switching-means which are arranged to place the handpieces on stand-by to receive operating media upon extraction of the handpieces from the storage device. The control arrangement includes supply sleeves having ducts for supplying operating media to both types of handpiece, couplings for releasably coupling the supply sleeves to the handpieces, and a foot-operated device for regulating the supply of operating media to the handpieces and including first switching-means for controlling the supply of air to drive the motor of the dental handpiece and second switching means for controlling the supply of spray to the dental handpiece.

3 Claims, 4 Drawing Figures

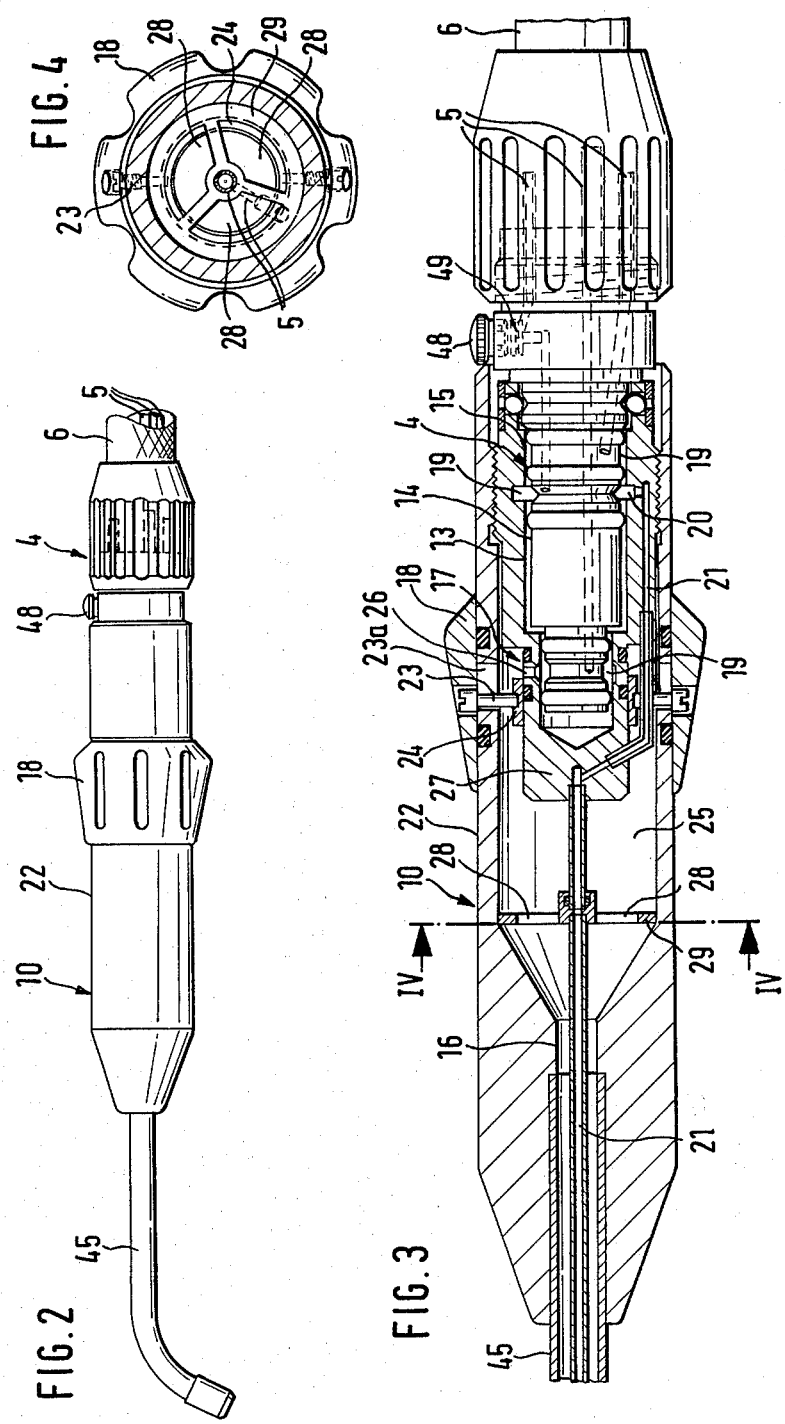

DENTAL HANDPIECES WITH SUPPLIED OPERATING MEDIA

This invention relates to a dental treatment installation comprising at least one dental handpiece having an air-operated drive motor and at least one outlet for discharging operating media used for dental purposes, such as cooling and/or rinsing media, a spray handpiece having a spray outlet for discharging a spray composed of water, or water and air, a control arrangement for controlling the supply of operating media to the handpieces, a storage device for the handpieces having storage-switching means which are arranged to place the handpieces on stand-by to receive operating media upon extraction of the handpieces from the storage device, an operator-controlled device for regulating the supply of operating media to the handpieces and including first switching means for controlling the supply of air to drive the motor of the dental handpiece and second switching means for controlling the supply of spray to the dental handpiece, supply sleeves having ducts for supplying operating media to the handpieces, and couplings for releasably coupling the supply sleeves to the handpieces.

Dental handpieces with an air-driven tool, for example a drill, can be, for example, air turbine or air motor handpieces. Several spray handpieces can also be provided in place of only one spray handpiece. Moreover, in place of or as well as water, another liquid, e.g. a medicating liquid, can also be fed to the handpieces.

A device of the above-named type is known from the publication "Kabo DYNAMICA 1033" from the firm Kaltenbach & Voigt. In the case of this known device, the spray handpiece which is practically unreleasably connected to its supply sleeve, is provided in a way known from German Patent Specification No. 20 41 503 and German Offenlegungschrift 25 49 177 with two push switches which are manually operable from the exterior, of which, for example, one, when operated, releases cooling or rinsing air and the other, when operated, releases cooling or rinsing water. If both push switches are operated simultaneously, a mixture of air and water can be released as a spray.

The arrangement of the two push switches makes a relatively thick and unwieldy design of the spray handpiece necessary, with the result that the dentist is obliged to adjust his grip to a large extent when transferring from a relatively slim dental handpiece to the spray handpiece. Added to this is the considerable inconvenience that he is obliged to make yet another adjustment, this time in respect of the manner in which he operates the handpiece. When working with a dental handpiece, which is generally held in the hand like a pencil, the dentist can control, in a manner to which he is accustomed, all functions of the handpiece, e.g. turning the tool or making other movements, by confortably operating the appropriate switching means of the foot-control device, by operating the switching means for drive air, by using the mixture of air and water leaving the tool end of the handpiece as a spray, or using a flow of air leaving the tool end of the handpiece as a fragment dispersal air-flow, whereas on the other hand, when working with the spray handpiece, the dentist must change over to the said hand-operation of the push switch provided on the spray handpiece, which also generally necessitates a different grip.

In the case of the device according to German Offenlegungschrift No. 25 49 177, it is possible to connect handpieces of various types, therefore spray handpieces included, to one and the same supply sleeve with the aid of releasable couplings. This device, however, has all the above-mentioned disadvantages due to the spray handpiece being provided with the two manually operable push switches.

A device is known from German Offenlegungschrift No. 20 21 540, with which it is possible to operate and respectively regulate both the dental handpieces and the spray handpiece, designed here without switches, with the same foot-control device. The spray handpiece is, however, unreleasably connected to its supply sleeve supplying only spray-air and only spray-water, which has the result that a normal foot-control device for air-driven dental handpieces can not be used, but that the foot-control device—so that it can be used for dental handpieces and for spray handpieces alike—must have a quite specific design, in order that the respectively desired functions may be regulated. This necessitates high technical expenditure.

The invention has been developed primarily, though not exclusively, with a view to achieve the aim of creating an installation of the above type, with which, avoiding a change-over for the dentist when transferring from a dental handpiece to a spray handpiece, it is possible to use one and the same foot-control device, and at that a conventional foot-control device for air-driven dental handpieces, for operating or respectively regulating both the dental handpieces and the spray handpieces, without this conventional foot-control device needing to be modified or specially designed in any way.

Accordingly, the invention provides a dental installation comprising at least one dental handpiece having an air-operated drive motor and at least one outlet for discharging operating media used for dental purposes, such as cooling and/or rinsing media; a spray handpiece having a spray outlet for discharging a spray composed of water, or water and air; a control arrangement for controlling the supply of operating media to the handpieces; and a storage device for the handpieces having storage-switching means which are arranged to place the handpieces on stand-by to receive operating media upon extraction of the handpieces from the storage device, in which:

the control arrangement includes supply sleeves having first, second and third ducts for supplying to the handpieces respectively cooling or rinsing air, drive air for the motor of the dental handpiece, and water, and couplings for releasably coupling the supply sleeves to the handpieces; and an operator-controlled device for regulating the supply of operating media to the handpieces and including first switching means for controlling the supply of air to drive the motor of the dental handpiece and second switching means for controlling the supply of spray, composed of cooling or rinsing air, or cooling or rinsing water, to the dental handpiece, and in which:

each coupling comprises a first coupling member connected to one of the handpieces and a second coupling member connected to a respective one of the supply sleeves, said supply sleeve being capable of supplying operating media, under the control of said operator-controlled device, to the dental handpiece or to the spray handpiece, as desired, whenever the handpiece is coupled-up to any one of the supply sleeves via a respective coupling; and said first coupling member connected to the spray handpiece includes (a) means for blocking said first duct of any supply sleeve to which it is coupled in order to prevent the supply of the cooling or rinsing air to the spray handpiece, (b) connecting means for connecting said second duct of any supply sleeve to which it is coupled in order to supply water to the spray outlet of the spray handpiece, (c) means communicating with said third duct of any supply sleeve to which it is coupled in order to supply water to the spray outlet of the spray handpiece and (d) an external operating means provided on the spray handpiece for preventing the supply of air to the spray outlet as and when required.

The advantages achieved by the invention are to be seen essentially in that the spray handpiece, which can be coupled as desired to any supply sleeve, which are connected together to one and the same foot-control device of a conventional dental supply device, now no longer has two manually operable push switches, and therefore can be designed to be relatively slim, in more or less the same manner as a dental handpiece, and can therefore be held like the latter in the manner of a pencil, whereby added to this is the fact that only one foot-control device is needed, and at that a foot-control device of a conventional type, due to the particular design of the handpiece coupling members with locking elements closing off the working media ducts for unrequired media, so that, when transferring from the one type of handpiece to the other, the dentist does not need to change position at all, not only in respect of holding the dental and spray handpiece, that is from the point of view of grip, but also in respect of regulating the supply of working media, that is regarding manner of operation. Due to the particular design of the coupling members, the drive air, otherwise serving the purpose of driving the dental handpiece, is now available in the spray handpiece as very effective spray-air, and, when mixed with spray-water, as a spray, whereby the discharge intensity of this spray-air—just as otherwise the rotary speed of the tool of the dental handpiece—can be regulated by operating the drive-air switching means of the foot-control device. If the switching member of the spray handpiece is operated, the spray handpiece can also release spray-water alone instead of spray. Since, for this purpose, only a single switching member, respectively a single locking member to close off the spray-air duct is necessary, no, or practically no increase in dimensions, particularly of the diameter of the spray handpiece, is necessary, with the result that the dentist holding the light and slim spray handpiece like a dental handpiece in the manner of a pencil, can operate the switching member comfortably with one finger, preferably with the thumb.

When work is to be carried out with the spray handpiece, then, after taking hold of the spray handpiece, the dentist or his assistant needs to operate the switching means for spray only on the foot-control device, whereby the cooling, or rinsing air supplied otherwise to the dental handpiece to make a spray is closed off by the locking element of the coupling member of the spray handpiece. The cooling or respectively rinsing water, on the other hand, reaches the spray handpiece. If, now, the switching means for drive-air is operated on the foot-control device, the drive-air reaches the spray handpiece as spray-air, whereby its escape from a spray channel, either by itself or mixed with the said water, can be regulated in a simple manner by the said switching member on the spray handpiece.

BRIEF DESCRIPTION OF THE DRAWINGS

FIG. 2 is a side view of a spray handpiece of the installation, with an attached sleeve for supply operating media to the spray handpiece;

FIG. 3 is a sectional view, to an enlarged scale, of the spray handpiece shown in FIG. 2; and FIG. 4 is a section taken on the line IV—IV in FIG. 3.

DESCRIPTION OF PREFERRED EMBODIMENT

Figure 1:
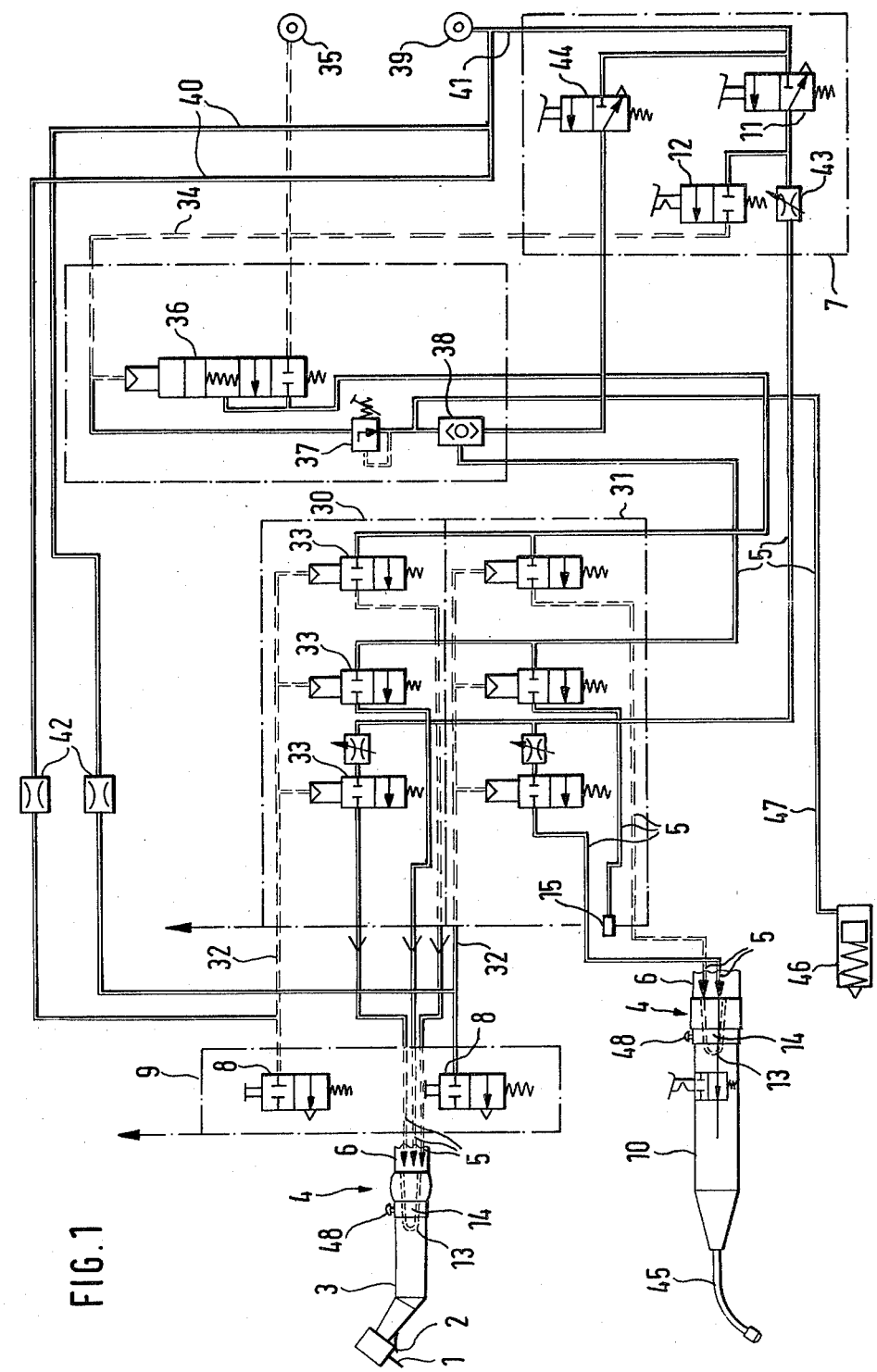
FIG. 1 is a schematic representation of a dental treatment installation in the form of a pneumatic circuit diagram.

Referring now to the drawings, there is shown a dental treatment installation comprising one or more dental handpieces, a spray handpiece, and a control arrangement for controlling the supply of operating or working media to the handpieces.

A device for supplying working media (consisting of water and air) to dental handpieces 3 having an air-driven tool 1, e.g. a drill, and at least one nozzle-like outlet aperture 2 for cooling or rinsing means directed on to the tool 1, comprises supply sleeves 6 containing ducts 5, for the working media, which lead to the handpieces 3 and are releasably connected to the latter by a coupling 4, and an operator controlled device in the form of a foot-control device 7 for regulating the supply of working media to the dental handpieces 3 which can be switched on to stand-by, when taken out of a storage device 9, by storage switching means 8.

In addition to supplying working media to the dental handpieces 3, the device also supplies air and/or water to a spray handpiece 10.

The foot control device 7 has first switching means 11 for regulating drive air fed to the dental handpiece 3, and second switching means 12 for regulating spray, which is formed by cooling or rinsing air fed to the outlet aperture 2 of the dental handpiece 3 with the aid of the ducts 5, and cooling or rinsing water fed there. The couplings 4 consist respectively of coupling members 13, 14, a first one connected to the dental handpiece 3 and a second connected to supply sleeve 6.

It can be seen from the drawing that the spray handpiece 10 is releasably connected, likewise by a coupling 4 with two coupling members 13, 14, to a supply sleeve 6 adapted also to supply the dental handpiece 3 and connected to the foot-control device 7. To this extent, all the coupling members 14 of the supply sleeves 6 are designed in the same way. It can be seen particularly from FIG. 3 that the coupling member 13 of the spray handpiece 10 is provided with blocking means in the form of a locking element 15, which closes off a first working media duct 5 for cooling or rinsing air of the supply sleeve 6 when connected to the coupling member 14 of the supply sleeve 6, and with connecting means in the form of a connecting element 17 connecting a second working media duct 5 (which normally supplies drive air to dental handpiece 3) of the supply sleeve to the spray-air duct 16 of the spray handpiece 10 and it can be seen further that the spray handpiece 10 is provided with an externally operable switching member 18 to close off the spray-air duct 16 as required.

The coupling member 13 of the handpieces 3, 10 is formed by an insert aperture provided on the end of the handpiece away from the tool 1, into which aperture the coupling member 14 of the respective supply sleeve 6 designed, for example, as a flexibly engageable plug can be inserted. The locking element 15 is formed by a wall section of the insert aperture forming the coupling member 13. The working media duct 5 for cooling or rinsing air runs—just as the other ducts 5 for cooling or rinsing water and for drive air—approximately axially through the coupling member 14 formed by the plug, out of which each of the ducts 5 open radially into a respective one of three outer annular channels 19. An inlet aperture 20 of the spray-water duct 21 of the spray handpiece 10 is associated with the annular channel 19 associated with a third one of ducts 5 so as to accommodate the cooling or rinsing water. The spray-water duct 21 is held inside the spray handpiece 10 with the help of a centering disc 29 with passages 28 for the spray air.

The switching member 18 is designed as a switching annulus which is axially displaceable on the exterior of the grip sleeve 22 of the spray handpiece 10, and which is connected by means of at least one extension 23 directed radially inwards through at least one perforation 23a of the grip sleeve 22, to a blocking member 24, which locks in the closed position a through aperture 26 of the spray-air duct 16 opening into an overflow space 25 of the spray handpiece 10 and forming the connecting element 17. The through aperture 26 of the spray-air duct 16 thereby opens radially from the interior of the handpiece into the overflow space 25. The locking member 24 is designed as an annular slide plate, which encloses a cylindrical portion 27 of the spray-air duct 16 having the through aperture 26 and which is adapted to be closed off in a down-flow direction.

The device according to FIG. 1 has a switching block 31 for the spray handpiece 10, which can be switched on to stand-by by storage switching means 8—like the dental handpiece 3—and a switching block 30 for the dental handpiece 3. As shown by the broken arrows pointing upwards in FIG. 1, several storage devices 9 and several switching blocks 30, 31 can be arranged adjacent to each other.

The switching blocks 30, 31 have, for each working medium, a switching valve 33, controllable by a control line 32, preferably by an air-control line, from the storage switching means 8, for switching the handpieces 3, 10 on to stand-by.

The device according to FIG. 1 also has a spray control block 34, which is connected to a water source 35, and a pneumatically operable water valve 36, from which the working media duct 5 for water originates. The spray control block 34 also has a pressure-reducing valve 37 for spray air, i.e. for cooling or rinsing air, and a double air-check valve 38.

A compressed air source is indicated with 39, from which on the one hand, supply lines 40 lead to the air-control lines 32, and on the other hand, the supply line 41 is fed to the foot-control device 7. Choke valves 42 are arranged in the supply lines 40.

In FIG. 1, the locking element 15 closing off the cooling or rinsing air duct 5 is shown by a small box. A pressure-reducing choke is indicated with 43.

As long as the handpieces 3, 10 are in the storage device 9, the control lines 32 are under pressure and the control valves 33 are closed.

If the dental handpiece 3 is removed from the storage device 9, then the storage switching means 8 effect an opening of the control valves 33 of the switching block 30. By operating the switching means, drive-air now reaches the dental handpiece 3. If the switching means 12 for spray, i.e. for cooling or rinsing air and cooling or rinsing water, is operated, then the latter media pass through the appropriate ducts 5 to the dental handpiece 3. The switching means 12 is suitably designed as a preselect-switching means, so that, once it has been operated, both drive air and cooling or rinsing air and cooling or rinsing water are released when the switching means 11 is operated. A switching means 44 for switching on blast air alone, which escapes from the outlet aperture 2 as a fragment dispersal air-flow, is also provided on the foot-control device 7.

If the spray handpiece 10 is taken out of the storage device 9, then the appropriate storage switching means 8 effect the opening of the switching valves 33 of the switching block 31. When the switching means 12 for spray is operated, only cooling or rinsing water is released, since the release of cooling or rinsing air is prevented by the locking element 15. If the main switching means 11 is operated, then cooling or rinsing water and drive air reach the spray handpiece 10 as spray-water and spray-air, and they leave the channels 45 of the spray handpiece as a mixture, or a spray. If the dentist wishes only water to escape from the channels 45, he needs only to operate the switching member 18 of the spray handpiece 10.

The handpieces 3 and 10 visible in FIG. 1 can be exchanged with each other without the above-described method of operation being thereby influenced.

A spray-indicating element is indicated by 46, which is connected to the spray control block 34 via a line 47, and which indicates the preselected release of spray for example by an optical color signal.

Another water regulating device 49 with a regulating screw 48 is provided on the coupling member 14 of the supply sleeve 6, whereby the water pressure can also be adjusted. This water-regulating device, however, only serves the purpose of exactly dosing the spray leaving the outlet aperture 2 of the dental handpieces 3. When the shown device is in operation, the regulating screw 48 is opened as far as possible, at least when the coupling member 14 is connected to the coupling member 13 of the spray handpiece 10.

If the spray handpiece 10 has, in a manner which is known in itself and is not shown, a heating device, for warming the current of cooling or rinsing air, in order for example to enable tooth cavities to be dried particularly effectively, then a pneumatically operating membrane contact switch can be built into the spray handpiece 10, which switch switches on the heating device as long as the air current is passing through the spray handpiece.

We claim:

1. A dental treatment installation comprising at least one dental handpiece having an air-operated drive motor and at least one outlet for discharging operating media used for dental purposes, such as cooling and/or rinsing media; a spray handpiece having a spray outlet for discharging a spray composed of water, or water and air; a control arrangement for controlling the supply of operating media to the handpieces; and a storage device for the handpieces having storage-switching means which are arranged to place the handpieces on stand-by to receive operating media upon extraction of the handpieces from the storage device, in which:

the control arrangement includes supply sleeves having first, second and third ducts for supplying to the handpieces respectively cooling or rinsing air, drive air for the motor of the dental handpiece, and water, and couplings for releasably coupling the supply sleeves to the handpieces; and an operator-controlled device for regulating the supply of operating media to the handpieces and including first switching means for controlling the supply of air to drive the motor of the dental handpiece and second switching means for controlling the supply of spray, composed of cooling or rinsing air, or cooling or rinsing water, to the dental handpiece, and in which:

each coupling comprises a first coupling member connected to one of the handpieces and a second coupling member connected to a respective one of the supply sleeves, said supply sleeve being capable of supplying operating media, under the control of said operator-controlled device, to the dental handpiece or to the spray handpiece, as desired, whenever the handpiece is coupled-up to any one of the supply sleeves via a respective coupling; and said first coupling member connected to the spray handpiece includes (a) means for blocking said first duct of any supply sleeve to which it is coupled in order to prevent the supply of the cooling or rinsing air to the spray handpiece, (b) connecting means for connecting said second duct of any supply sleeve to which it is coupled in order to supply said drive air to the spray outlet of the spray handpiece, (c) means communicating with said third duct of any supply sleeve to which it is coupled in order to supply water to the spray outlet of the spray handpiece (d) an external operating means provided on the spray handpiece for preventing the supply of air to the spray outlet as and when required, said external operating means comprising an annular switching device which is axially displaceable on the exterior of the spray handpiece; and including a radially inwardly extending projection provided on the annular switching device, an opening formed in the spray handpiece through which said projection extends, and a blocking member constituting said connecting means and arranged in the spray handpiece to be engaged by said projection for movement between opened and closed positions relative to a passage for the flow of drive air through the spray handpiece.

2. A dental treatment installation according to claim 1, in which said passage includes a spray-air duct having an aperture which opens radially from the interior of the handpiece into an overflow space and which is closable by said blocking member.

3. A dental treatment installation according to claim 2, in which said blocking member comprises an annular slide plate arranged on a hollow cylindrical member which defines part of said passage and has said aperture provided therein, said cylindrical portion being closed-off in a downflow direction.

* * * * *